US00PP22164P2

(12) United States Plant Patent
Hanes

(10) Patent No.: US PP22,164 P2
(45) Date of Patent: Sep. 27, 2011

(54) ***PETUNIA* PLANT NAMED 'WHIP AMTH'**

(50) Latin Name: *Petunia hybrida*
Varietal Denomination: Whip Amth

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 158 days.

(21) Appl. No.: 12/653,686

(22) Filed: Dec. 17, 2009

(51) Int. Cl.
*A01H 5/00* (2006.01)

(52) U.S. Cl. ..... Plt./356.19; Plt./356.13

(58) Field of Classification Search ..... Plt./356.19
See application file for complete search history.

(56) References Cited

U.S. PATENT DOCUMENTS

PP16,804 P2 * 7/2006 Iwaki et al. ..... Plt./356.22
PP17,291 P2 * 12/2006 Oud ..... Plt./356.18

OTHER PUBLICATIONS

UPOV ROM GTITM Computer Database, GTI Jouve Retrieval Software 2011/01 "CA" Citation for 'Whip Amth'.*

* cited by examiner

*Primary Examiner* — Wendy C Haas
(74) *Attorney, Agent, or Firm* — S. Matthew Edwards

(57) ABSTRACT

A new *Petunia* plant named 'Whip Amth' particularly distinguished by the medium sized purple-violet flowers, early blooming, good floriferousness, initially semi-compact and then an outwardly spreading plant habit.

1 Drawing Sheet

Latin name of the genus and species of the plant claimed: *Petunia hybrida.*

Varietal denomination: 'Whip Amth'.

BACKGROUND OF THE NEW PLANT

The present invention comprises a new *Petunia,* botanically known as *Petunia hybrida,* and hereinafter referred to by the variety name 'Whip Amth.'

'Whip Amth' is a product of a planned breeding program. The new cultivar has medium sized purple-violet flowers, is early blooming, good floriferousness, initially semi-compact and then an outwardly spreading plant habit.

'Whip Amth' originated from a open pollinated cross made in August 2005 in Gilroy Calif. The female parent was a commercially available variety designated 'Keiametsum,' U.S. Plant Pat. No. 16,804, with red-purple flower color, shorter internodes, longer ad lighter green foliage.

The male parent of 'Whip Amth' is unknown. The seed was sown in January 2006.

'Whip Amth' was selected as one flowering plant within the progeny of the stated cross in April 2006 the in a controlled environment in Gilroy, Calif.

The first act of asexual reproduction of 'Whip Amth' was accomplished when vegetative cuttings were propagated from the initial selection in April 2006, in a controlled environment in Gilroy, Calif.

BRIEF SUMMARY OF INVENTION

Horticultural examination of plants grown from cuttings of the plant initiated in April 2006, and continuing thereafter, has demonstrated that the combination of characteristics as herein disclosed for 'Whip Amth' are firmly fixed and are retained through successive generations of asexual reproduction.

'Whip Amth' has not been observed under all possible environmental conditions. The phenotype may vary significantly with variations in environment such as temperature, light intensity and day length.

A Plant Breeder's Right for this cultivar was applied for in Canada on Jan. 30, 2009. 'Whip Amth' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'Whip Amth' with colors being as true as possible with an illustration of this type.

Figure 1:
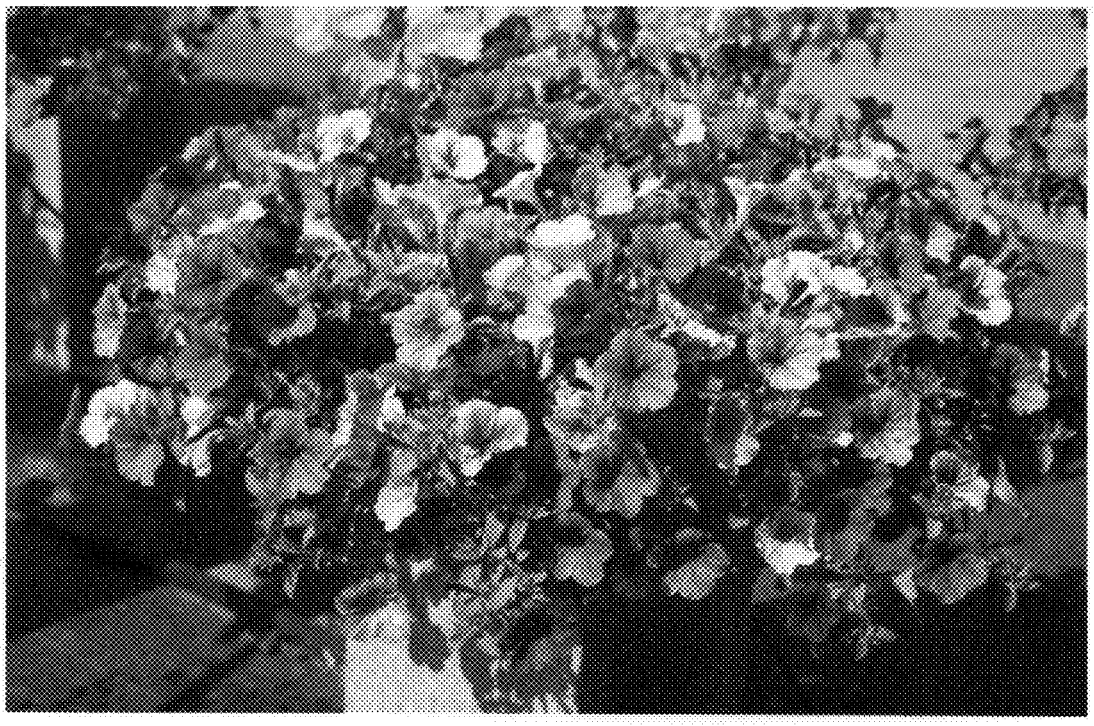
Figure 2:
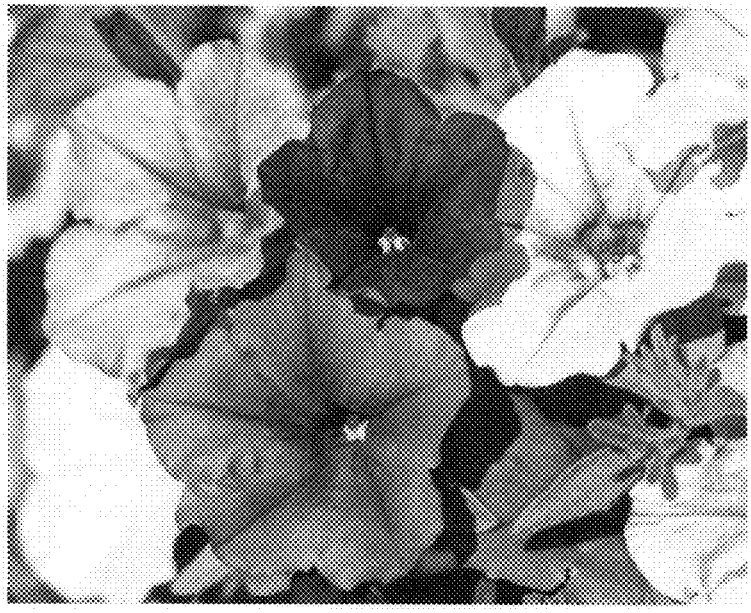

The photographic drawing shows in FIG. 1 three flowering potted plants of the new variety, and in FIG. 2, a close-up of the flowers.

DETAILED BOTANICAL DESCRIPTION

The plant descriptions, measurements and aforementioned photographs were taken in Gilroy, Calif. early September 2009, from plants growing outside in 10 inch basket trials, 3 plants per basket. These plants were approximately 15 weeks of age.

Color references are made to The Royal Horticultural Society Colour Chart (R.H.S.) 2001.

TABLE 1

DIFFERENCES BETWEEN THE NEW VARIETY 'WHIP AMTH' AND A SIMILAR VARIETY

| | 'Whip Amth' | 'Petlavve' (U.S. Pat. No. 17,291) |
|---|---|---|
| Internode length: | Longer | Shorter |
| Foliage color: | Medium green | More yellow-green |
| Sepal length: | Shorter | Longer |
| Flower color: | Purple-violet | Purple |

Plant:
*Form, growth and habit.*—Initially semi-compact to outwardly spreading, strong vigorous habit, well branched, early and continuous flowering.
*Plant height.*—14-16 cm.
*Plant height (inflorescence included).*—About 20 cm.
*Plant width.*—About 50 cm.
*Garden performance and tolerance to weather.*—Very good.
*Crop time to flowering.*—About 8 weeks.

Roots:
*Number of days to initiate roots and produce a rooted cutting.*—18-23 days at about 22 degrees C.
*Type.*—Fine, fibrous, free branching.
*Color.*—RHS N155B but whiter.

Foliage:
*Arrangement.*—Alternate, upper leaves sub-opposite.
*Immature, leaf color, upper surface.*—Closest to RHS 137A.
*Lower surface.*—Closest to RHS 146B.
*Mature, leaf color, upper surface.*—Closest to RHS 137A but a little lighter.
*Lower surface.*—Closest to RHS 146B.
*Length.*—3.5-3.6 cm.
*Width.*—1.8-2.3 cm.
*Shape.*—Ovate to broadly elliptical.
*Base shape.*—Attenuate.
*Apex shape.*—Acute.
*Margin.*—Entire.
*Texture, upper surface.*—Hirsute; glandular hairs.
*Lower surface.*—Hirsute; glandular hairs.
*Color of veins, upper surface.*—RHS 144A.
*Color of veins, lower surface.*—RHS 144A.
*Petiole color.*—RHS 144A.
*Length.*—0.1-0.2 cm.
*Diameter.*—0.2 cm.
*Texture.*—Hirsute; glandular hairs.

Stem:
*Color of stem.*—Between RHS 144A and RHS 144B.
*Length of stem.*—60-70 cm.
*Diameter.*—0.3 cm.
*Length of internodes.*—3.5-4.0 cm.
*Texture.*—Hirsute; glandular hairs.
*Color of peduncle.*—RHS 144A.
*Length of peduncle.*—1.0-2.3 cm.
*Peduncle diameter.*—0.15 cm.
*Texture.*—Hirsute; glandular hairs.

Inflorescence:
*Type.*—Flowers appear solitary in upper leaf axis. Floret type: Funnel-shaped; 5 lobed petals; fused at the base; calyx, 5 deeply lobed sepals.
*Blooming habit.*—Continuous throughout the growing season; Good floriferousness.
*Quantity of inflorescences per plant.*—About 35-45.
*Lastingness of individual blooms on the plant.*—About 4-8 days.
*Fragrance.*—None.

Bud: (Just before opening/showing color)
*Color.*—RHS N144D with a hint of RHS 182C at the apex end.
*Length.*—1.7-2.0 cm.
*Width.*—0.3-0.4 cm.
*Shape.*—Oblong.

Immature inflorescence:
*Diameter.*—4.0-4.2 cm.
*Color, upper surface.*—Closest to RHS N81A but a darker brighter and more velvety violet color.
*Lower surface.*—RHS N81C with RHS N81B at the margins.

Mature inflorescence:
*Floret horizontal diameter.*—4.6-4.8 cm.
*Vertical depth.*—4.0-4.5 cm.
*Petal color, upper surface.*—Closest to RHS N81A, maturing and fading to a RHS 155C background with patches of RHS N80A and RHS N78A at the margins, RHS N81a and N81B veining more heavily at the throat opening.
*Lower surface.*—RHS 155C ground color with patches of RHS N80B between the apices and margins.
*Petal apex shape.*—Obtuse.
*Petal base shape.*—Fused.
*Petal margin.*—Entire.
*Waviness of petals.*—Moderate.
*Petal lobation.*—Moderate.
*Petal texture, upper surface.*—Papillose.
*Under surface.*—Hirsute; glandular hairs along the mid-veins and basally.
*Corolla tube color inside.*—RHS 155B with RHS N80B veins.
*Outside.*—RHS 155C, slight striations of RHS N81C and RHS 157C mid-veins
*Corolla tube length.*—3.0 cm.
*Corolla texture, inside.*—Papillose.
*Outside.*—Hirsute; glandular hairs.

Calyx:
*Color, upper surface.*—RHS 137A.
*Lower surface.*—RHS 137A.
*Length.*—1.3-1.5 cm.
*Width.*—0.3-0.5 cm.
*Shape.*—Broadly ligulate.
*Apex shape.*—Acute.
*Based.*—Fused.
*Margins.*—Entire.
*Texture, upper surface.*—Hirsute; many glandular hairs.
*Lower surface.*—Hirsute; many glandular hairs.

Reproductive organs:
*Pistil.*—1.
*Length.*—2.1 cm.
*Style color.*—RHS 150C.
*Style length.*—1.7-1.9 cm.
*Stigma color.*—RHS 144A.
*Ovary color.*—RHS 151 A.
*Stamens.*—5.
*Color of filaments.*—RHS 155C with striations of RHS 71B towards the apex.
*Length filaments.*—2-2.1 cm.
*Anther color.*—RHS 158D.
*Anther length.*—0.1-0.15 cm.
*Anther shape.*—Reniform.
*Color of pollen.*—RHS 158C.
*Pollen amount.*—Moderate.
*Fertility/seed set.*—Has not been observed on this hybrid.

Disease/pest resistance: Has not been observed on this hybrid

What is claimed is:

1. A new and distinct variety of *Petunia* plant named 'Whip Amth,' substantially as illustrated and described herein.

* * * * *